United States Patent [19]

Sawa

[11] 4,042,592
[45] Aug. 16, 1977

[54] NOVEL DIBENZO[a,g]QUINOLIZINIUM COMPOUNDS

[75] Inventor: Yoshio Sawa, Nishinomiya, Japan

[73] Assignee: Kanebo, Ltd., Tokyo, Japan

[21] Appl. No.: 573,786

[22] Filed: May 1, 1975

[30] Foreign Application Priority Data

| May 8, 1974 | Japan | 49-51459 |
|---|---|---|
| May 8, 1974 | Japan | 49-51460 |
| May 9, 1974 | Japan | 49-51804 |
| May 9, 1974 | Japan | 49-51805 |
| May 9, 1974 | Japan | 49-51806 |
| May 11, 1974 | Japan | 49-52575 |
| May 11, 1974 | Japan | 49-52576 |
| May 11, 1974 | Japan | 49-52577 |
| May 11, 1974 | Japan | 49-52578 |
| May 11, 1974 | Japan | 49-52579 |
| May 14, 1974 | Japan | 49-54008 |
| May 14, 1974 | Japan | 49-54009 |
| May 14, 1974 | Japan | 49-54010 |
| May 14, 1974 | Japan | 49-54011 |
| May 14, 1974 | Japan | 49-54012 |

[51] Int. Cl.² .......................................... C07D 215/10
[52] U.S. Cl. ........................ 260/286 Q; 260/287 D; 260/287 C; 424/258
[58] Field of Search ................... 260/286 Q, 287 D

[56] References Cited

U.S. PATENT DOCUMENTS

| 3,341,544 | 9/1967 | Melzer et al. | 260/286 Q |
| 3,483,206 | 12/1969 | Weiner | 260/287 D |
| 3,565,899 | 2/1971 | Doebel et al. | 260/286 Q |
| 3,920,665 | 11/1975 | Shimada et al. | 260/286 Q |

FOREIGN PATENT DOCUMENTS

| 4,540,318 | 1970 | Japan | 260/286 Q |

OTHER PUBLICATIONS

Tet. Let. No. 11 pp. 803–806 (1973).

Primary Examiner—Delbert R. Phillips
Attorney, Agent, or Firm—Haight & Huard

[57] ABSTRACT

9-Hydroxydibenzo[a,g]quinolizinium compound of the formula:

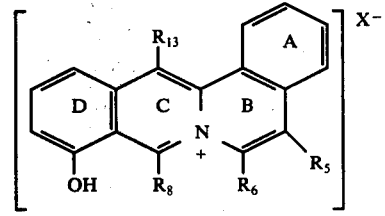

wherein $R_5$, $R_6$, $R_8$ and $R_{13}$ are each hydrogen or lower alkyl, and $X^-$ is a pharmaceutically acceptable anion. Additional substituent may be present on ring A and D. Betaines and 9-acylates are also provided. They inhibit growth of transplanted sarcoma or leukemia strains into mice.

16 Claims, No Drawings

NOVEL DIBENZO[A,G]QUINOLIZINIUM COMPOUNDS

This invention relates to a new class of dibenzo[a,g] quinolizinium compounds and method of synthesis of same. Berberine is an alkaloid found in *phellodendron amurense, Coptis japonica* or other plants, and has been used as intestinal antiseptics and the like.

It has attracted interest by chemists for the synthesis of analogues thereto and also by pharmacologists for various pharmacological properties thereof.

Thus, a number of derivatives of berberine have been synthesized and tested on their pharmacological properties. It has been reported that some of such derivatives have a tranquillizing or anti-tumor activity. Although anti-tumor activity of berberine itself has been known to be very weak, berberine has still remained to be of interest among other plant alkaloids having anti-tumor activity when a wide variety of its pharmacological acitvities are taken into consideration.

Most of hitherto tested berberine derivatives have a berbine nucleus as the parent structure whose 5 and 6 positions have been saturated. However, it is noteworthy that 2,3,10,11-tetramethoxy-8-methyl-5, 6-dehydroberbinium chloride known as coralyne has a strong antileukemia activity whose parent structure is unsaturated at its 5 and 6 positions.

The present invention provides a new class of dibenzo[a,g] quinolizinium compounds whose parent rings are unsaturated at 5 and 6 positions.

The compounds of the present invention may be represented by the following formula:

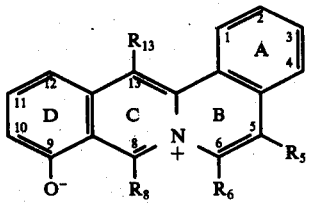

I wherein $R_5$, $R_6$, $R_8$ and $R_{13}$ are each hydrogen atom or lower alkyl; positions 1 to 4 and 10 to 12 on ring A and ring D respectively are each substituted with 0 to several substituents selected from the group consisting of lower alkyl, hydroxy, lower alkoxy, lower alkylenedioxy, amino and lower alkylamino; with the proviso that when $R_8$ is hydrogen atom and ring D is substituted only at positions 2 and 3 with alkoxy or alkylenedioxy.

The present invention also includes pharmaceutically acceptable acid-addition salts of the formula:

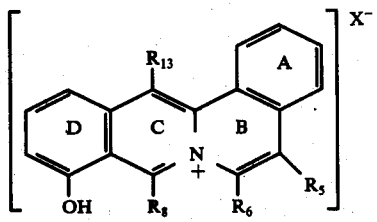

II wherein symbols $R_5$, $R_6$, $R_8$, and $R_{13}$ and ring A and D are as defined above, and $X^-$ represents an anion of pharmaceutically acceptable acid, and 9-O-acylates of the formula:

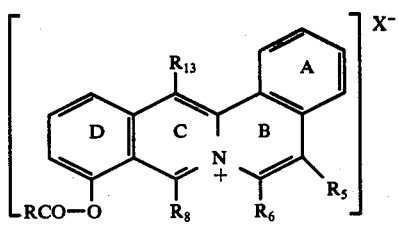

III wherein ring A, D and symbols $R_5$, $R_6$, $R_8$, $R_{13}$ and $X^-$ are as defined above, and RCO is an acyl group.

The compounds of the present invention possess, as the parent nucleus, a dibenzo[a,g] quinolizinium structure whose 5 and 6 positions are unsaturated and whose nitrogen atom in the nucleus is quarternized to form either a betaine structure (Formula I) with the hydroxyl group at 9 position, or a quaternary ammonium salt (Formula II) with an anion such as halide, sulphate, phosphate, nitrate, acetate, propionate, fumarate or the like.

The compounds optionally have at positions 1 to 4 and 10 to 12 on ring A and D, one or more additional substituents.

Examples of said additional substituents are lower alkyl group such as methyl, ethyl or propyl; hydroxyl; lower alkoxy such as methoxy, ethoxy or propoxy; lower alkylenedioxy such as methylenedioxy or ethylenedioxy; amino, and lower alkylamino such as methylamino, ethylamino or propylamino.

When $R_8$ is hydrogen atom and ring D is substituted only at position 10 with alkoxy, ring A cannot be substituted only at positions 2 and 3 with alkoxy or alkylenedioxy.

The compounds of Formula I or II may be acylated to form the compounds of Formula III with an acyl group derived from aliphatic carboxylic acids such as acetic acid, propionic acid, or trichloroacetic acid, araliphatic carboxylic acids such as cinnamic acid, or dimethylcarbamic acid.

The parent substance in structure of compounds of the present invention is 9-hydroxydibenzo[a,g] quinolizinium betaine.

In addition to the 9-hydroxyl group, the compounds of the present invention may have one to several substituents as above either solely on ring A or D, or on both.

The present invention also relates to a method of the synthesis of compounds of Formula II above which comprises reacting isoquinoline-1-carbaldehyde or appropriately substituted derivatives thereof with 2-hydroxybenzyl halide, 2-benzyloxybenzyl halide or appropriately substituted derivatives thereof, and cyclizing the resulting intermediate.

Compounds capable of forming said isoquinoline-1-carbaldehyde or appropriately substituted derivatives thereof in situ such as oximes or acetals may be used.

The reaction may be represented, for example, by the following equation:

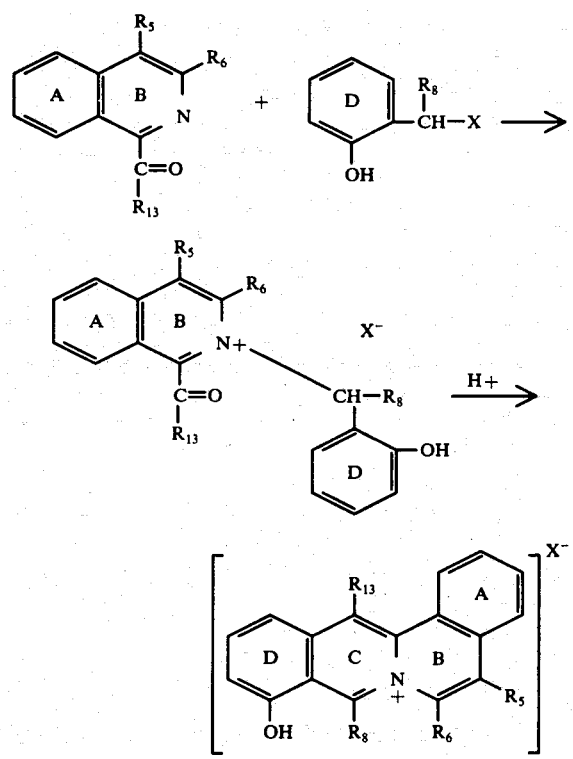

The first step of the reaction is preferably carried out by reacting the isoquinoline-1-carbaldehydes, oximes or acetals thereof with equimolar or slightly excessive amounts of the benzyl halides in a solvent, preferably in a polar solvent such as methanol, ethanol, acetone, methyl ethyl ketone, cyclohexanone, chloroform, dichlorethane, acetonitrile, propionitrile, benzonitrile, nitromethane, nitrobenzene, dimethylformamide, tetramethylenesulfone, tetrahydrofuran and the like at a temperature from 0° to 150° C, preferably from 20° to 60° C. The resulting benzyl isoquinolinium halides are cyclized into the corresponding dibenzo[a,g] quinolizinium halides of Formula II by heating said isoquinolinium halides in the pressence of a strong protonic acid such as sulfuric acid, phosphoric acid, hydrochloric acid, hydrofluoric acid, hydrobromic acid, or perchloric acid, preferably perchloric acid, hydrochloric acid, hydrobromic acid or the like at a temperature from 40° to 120° C, preferably from 50° to 100° C. Normality of the acid is preferably from 5N to 20N, more preferably from 8N to 15N. Polyphosphoric acid may be used also in the cyclizing step.

The 9-hydroxy dibenzo[a,g]quinolizinium halides of Formula II thus obtained may be converted, if desired, into other anionides or betaines, for example, by passing through a column of ion-exchange resins in accordance with conventional ion-exchange technique, or by treating with alkali.

The 9-acyloxydibenzo[a,g] quinolizinium anionides of Formula III may preferably be derived from the compounds of Formula I or II by acylating thereof with a reactive derivative of an appropriate acid.

Examples of said reactive derivative are acid halide such as chloride or bromide, or acid anhydride. The reaction may be carried out in an inert solvent such as chloroform, dichloromethane, acetonitrile, dimethylformamide, tetramethylenesulfone or the like preferably in the presence of an acid acceptor such as sodium hydroxide, sodium carbonate, pyridine, triethylamine and the like.

The compounds of the present invention effectively inhibit the growth of transplanted sarcoma or leukenia strain in standard laboratory animals.

Sarcoma strain S180 (ascitic type) was transplanted into the peritoneum of groups of mice each comprising six and test compound was administered intraperitoneally to mice once a day for 5 consecutive days.

After one week, abdominal ascites accumulate was collected and the total pack cell volume (TPCV) was measured. Inhibitory rate of growth of S180 was calculated by comparing the TPCV between treated and untreated control groups.

In like manner, increase in lifespan (ILS) of mice trans )lanted with Leukemia strain L 1210 was observed.

The results obtained are shown in the following table.

| Compound | Dose, mg/kg/day | Tumor Strain (TPCV) 8 mg | (ILS) 70 mg |
|---|---|---|---|
| 9-hydroxydibenzo[a,g] quinolizinium bromide | | 54% | 60.9% |
| 9-hydroxy-10-methoxydibenzo[a,g] quinolizinium bromide | | 100% | 240.7% |
| 9-hydroxy-11-methoxydibenzo[a,g] quinolizinium bromide | | 36.2% | 50.1% |
| 9-hydroxy-11-ethoxydibenzo[a,g] quinolizinium bromide | | 86.4% | 127.2% |
| 3,9-dihydroxy-10-methoxydibenzo [a,g] quinolizinium bromide | | 78.4% | 89.1% |
| 9,10-dihydroxy-3-methoxydibenzo [a,g] quinolizinium bromide | | 45.0% | 32.6% |
| 9-hydroxy-2, 10-dimethoxydibenzo [a,g] quinolizinium bromide | | 92.0% | 160.7% |
| 9-acetoxy-10-methoxydibenzo[a,g] quinolizinium bromide | | 100% | 210.0% |
| 9-hydroxy-10-methoxy-8-methyldibenzo [a,g] quinolizinium bromide | | 100% | >300% |
| 9-hydroxy-10-methoxy-13-methyldibenzo [a,g] quinolizinium bromide | | 100% | 274% |
| 9-hydroxy-8, 13-dimethyl-10-methoxy- dibenzo[a,g] quinolizinium bromide | | 100% | >300% |

The following examples will further illustrate the invention although it will be understood that the invention is not limited to these examples which are given by way of illustration and not limitation.

EXAMPLE 1

9-hydroxydibenzo[a,g] quinolizinium bromide

600mg. of 2-hydroxybenzyl bromide is added to a solution of 500mg. of isoquinoline-1-carbaldoxime and the mixture is stirred at 50°–60° C for 1 hour and at room temperature overnight successively. After removing small amounts of dimethylformamide (DMF) by evaporation, 30ml. of ethyl acetate is added to the reaction mixture and the resulting crystals of a quaternary ammonium salt are filtered off. The crystals are heated in 12ml. of 48% hydrobromic acid at 70° C for 2 hours with stirring. The resulting red crystals are filtered off. recrystallized from ethanol/ether. Yield 550mg. m.p. 212°–215° C (with decomposition).

2g. of the bromide thus obtained is added to 10ml. of 5% aqueous solution of potassium hydroxide. Then the mixture is stirred for 20 minutes at room temperature whereupon black crystals of 9-hydroxydibenzo[a,g] quinolizinium betaine is obtained. m.p. 248°–253° C (with decomposition). The betaine is dissolved in ethanol and dry hydrogen chloride gas is bubbled into the solution, whereby yellowish orange crystals 9-hydroxydibenzo[a,g] quinolizinium chloride are obtained. m.p. 220°–223° C (with decomposition).

In like manner, the following salts are prepared:

Nitrate, m.p. 231°–233° C (with decomposition),
Sulfate, m.p. 221°–223° C (with decomposition),
Phosphate, m.p. 210°–213° C (with decomposition),

EXAMPLE 2

9-acetoxydibenzo[a,g] quinolizinium chloride 2g. of 9-hydroxydibenzo[a,g] quinolizinium betaine is dissolved in 150ml. of chloroform while it is hot. To the solution is added 1.5 equivalents of acetyl chloride in 60ml. of chloroform.

The mixture is refluxed for 3 hours and cooled. The resulting crystals are filtered off and recrystallized from ethanol/ether.

Yield 1.8g. m.p. 202°–205° C (with decomposition).

EXAMPLE 3

9-hydroxy-10-methoxydibenzo[a,g] quinolizinium bromide

To a solution of 500mg. of isoquinoline-1-carbaldoxime in 10ml. of DMF is added 1.5g of 2-hydroxy-3-methoxybenzyl bromide. The mixture is stirred in a water-bath of a temperature of 60°–70° C for 1 hour and then at room temperature overnight. 50ml. of ether is added to the reaction mixture. The resulting crystals are filtered off and washed with ehter and ethyl acetate successively. The crystals are heated in 10ml. of 48% hydrobromic acid at 65° for 45 minutes with stirring.

The resulting red orange crystals are filtered off, recrystallized from methanol/ethyl acetate. Yield 600mg. m.p. 273°–274° C (with decomposition), 2-benzyloxy-3-methoxybenzyl bromide may be used instead of 2-hydroxy-3-methoxybenzyl bromide as in the above procedure with substancially equivalent results.

300mg. of 9-hydroxy-10-methoxydibenzo[a,g] quinolizinium bromide is dissolved in 5ml. of 5% aqueous solution of sodium hydroxide with stirring to give dark green crystals of 9-hydroxy-10-methoxydibenzo[a,g] quinolizinium betaine decomposing at 250°–253° C (chloroform).

The betaine is treated with methanolic HCl to give the corresponding chloride decomposing at 278°–279° C (methanol/ether).

In like manner, the following salts are obtained:

Nitrate, m.p. 261°–263° C (with decomposition),
Sulfate, m.p. 300° C (with decomposition),
Phosphate, m.p. 285°–286° C (with decomposition),

EXAMPLE 4

9-acetoxy-10-methoxydibenzo[a,g] quinolizinium chloride:

1g. of 9-hydroxy-10-methoxydibenzo[a,g] quinolizinium betaine is disseloed in 40ml. of chloroform. To the solution is added dropwise 1.5 times equivalents of acetyl chloride in 10ml. of chloroform under mild reflux. The mixture is refluxed for additional 2 hours. The reaction mixture is evaporated to dryness. The residue is washed with water and recrystallized from ethanol/ether.

Yield 1.01g., m.p. 198°–201° C (with decomposition).

In like manner, the following compounds are obtained: Trichloroacetic ester, m.p. 131°–135° C (with decomposition), Propionic ester, m.p. 213°–216° C (with decomposition).

EXAMPLE 5

2,10-dimethoxy-9-hydroxydibenzo[a,g] quinolizinium bromide:

To a solution of 500mg. of 7-methoxyisoquinoline-1-carbaldoxime in 10ml. of DMF is added 700mg. of 2-hydroxy-3-methoxybenzyl bromide.

The mixture is stirred in a water-bath of a temperature of 50°–60° C for 1 hour and then at room temperature overnight. 30ml. of ether is added to the reaction mixture. The resulting off-white crystals are filtered off, washed and heated in 8ml. of 48% hydrobromic acid at 65°–75° C for 1 hour with stirring. The resulting red orange crystals are filtered off and recrystallized from ethanol/ethyl acetate.

Yield 530mg., m.p. 195°–199° C (with decomposition).

2-benzyloxy-3-methoxybenzyl bromide is used instead of 2-hydroxy-3-methoxybenzylbromide with substantially equivalent results.

300mg. of 2,10-dimethoxy-9-hydroxydebenzo[a,g] quinolizinium bromide is dissolved in 5ml. of 5% aqueous solution of sodium hydroxide with stirring to give dark brown crystals of 9-hydroxy-2, 10-dimethoxydibenzo [a,g] quinolizinium betaine decomposing at 255°–258° C (chloroform).

The betaine is treated with methanolic HCl to give the corresponding chloride decomposition at 200°–203° C (ethanol/ether).

In like manner, the following salts are obtained:

Nitrate, m.p. 238°–240° C (with decomposition),
Sulfate, m.p. 245°–247° C (with decomposition),
Phosphate, m.p. 218°–220° C (with decomposition).

2g. of 2,10-dimethoxy-9-hydroxydibenzo-[a,g] quinolizinium betaine is dissolved in 80ml. of chloroform. To the solution is added dropwise 1.3 times equivalents of acetyl chloride in 20ml. of chloroform and the mixture is refluxed for 3 hours. After cooling, the resulting crystals are filtered off, and recrystallized from ethanol/ethyl acetate whereby orange crystals of 9-acetoxy-2,10-dimethoxydibenzo[a,g] quinolizinium chloride is obtained. Yield, 1.7 g.

The following esters are prepared by the above manner:

Propionic ester, m.p. 205°–208° C (with decomposition),
Trichloroacetic ester, m.p. 200°–203° C (with decomposition), In the following examples, the procedures of Example 5 are repeated except that appropriately substituted isoquinoline-1-carbaldoxime and appropriately substituted 2-hydroxy (or benzyloxy) benzyl halide are used as the starting materials.

EXAMPLE 6

2-ethoxy-9-hydroxy-10-methoxydibenzo[a,g] quinolizinium bromide, m.p. 190°–193° C (with decomposition);

Betaine, m.p. 240°–245° C (with decomposition),
Nitrate, m.p. 210°–213° C (with decomposition),
Sulfate, m.p. 222°–225° C (with decomposition),
Phosphate, m.p. 215°–218° C (with decomposition),
Chloride of acetic ester, m.p. 240°–242° C (with decomposition),
Chloride of propionic ester, m.p. 231°–233° C (with decomposition),
Chloride of trichloroacetic ester, m.p. 227°–230° C (with decomposition).

EXAMPLE 6

2-ethoxy-9-hydroxy-10-methoxydibenzo[a,g] quinolizinium bromide, m.p.190°–193° C (with decomposition);

Betaine, m.p. 240°–245° C (with decomposition),
Nitrate, m.p. 210°14 213° C (with decomposition),
Sulfate, m.p. 222°–225° C (with decomposition),
Phosphate, m.p. 215°–218° C (with decomposition),
Chloride of acetic ester, m.p. 240°–242° C (with decomposition),
Chloride of propionic ester, m.p. 213°–233° C (with decomposition),
Chloride of trichloroacetic ester, m.p. 227°–230° C (with decomposition).

EXAMPLE 7

2,9-dihydroxy-10-methoxydibenzo[a,g] quinolizinium bromide, m.p. 210°–215° C (with decomposition).

EXAMPLE 8

3,10-dimethoxy-9-hydroxydibenzo[a,g] quinolizinium bromide, M.P. 230°–233° C (with decomposition).

EXAMPLE 9

3-ethoxy-9-hydroxy-10-methoxydibenzo[a,g] quinolizinium bromide, m.p. 240°–243° C (with decomposition);

Betaine, m.p. 275°–280° C (with decomposition);
Chloride, m.p. 215°–219° C (with decomposition);
Nitrate, m.p. 230°–233° C (with decomposition);
Sulfate, m.p. 215°–217° C (with decomposition);
Phosphate, m.p. 209°–211° C (with decomposition);
Chloride of acetic ester, m.p. 250°–253° C (with decomposition);
Chloride of trichloroacetic ester, m.p. 241°–243° C (with decomposition).

EXAMPLE 10

3,9-dihydroxy-10-methoxydibenzo[a,g] quinolizinium bromide, m.p. 260°–263° C (with decomposition).

EXAMPLE 11

4,10-dimethoxy-9-hydroxydibenzo[a,g] quinolizinium bromide, m.p. 236°–239° C (with decomposition);

Betaine, m.p. 280°–285° C (with decomposition);
Chloride, mp. 252°–255° C (with decomposition);
Nitrate, m.p. 240°–244° C (with decomposition);
Sulfate, m.p. 218°–220° C (with decomposition);
Phosphate, m.p. 230°–233° C (with decomposition);
Chloride of acetic ester, m.p. 200°–203° C (with decomposition);
Chloride of trichloroacetic ester, m.p. 205°–209° C (with decomposition).

EXAMPLE 12

10-ethoxy-9-hydroxydibenzo[a,g] quinolizinium bromide, m.p. 202°–204° C (with decomposition);

Betaine, m.p. 245°–250° C (with decomposition);
Chloride, m.p. 221°–224° C (with decomposition);
Nitrate, m.p. 230°–232° C (with decomposition);
Sulfate, m.p. 220°–222° C (with decomposition);
Phosphate, m.p. 215°–217° C (with decomposition);
Chloride of acetic ester, m.p. 218°–220° C (with decomposition);
Chloride of trichloroacetic ester, m.p. 224°–227° C (with decomposition).

EXAMPLE 13

10-ethoxy-9-hydroxy-2-methoxydibenzo[a,g] quinolizinium bromide:

The procedures of Example 5 are repeated except that 7-methoxyisoquinoline-1-carbaldehyde and 3-ethoxy-2-hydroxy-benzyl bromide or 3-ethoxy-2-benzyloxybenzyl bromide are used as the starting materials.

m.p. 207°–210° C (with decomposition);
Betaine, m.p. 260°–265° C (with decomposition);
Chloride, m.p. 220°–224° C (with decomposition);
Nitrate, m.p. 230°–233° C (with decomposition);
Sulfate, m.p. 239°–242° C (with decomposition);
Phosphate, m.p. 215°–218° C (with decomposition);
Chloride of acetic ester, m.p. 215°–218° C (with decomposition);
Chloride of trichloroacetic ester, m.p. 230°–233° C (with decomposition).

EXAMPLE 14

Example 13 is repeated except that 7-ethoxy-isoquinoline-1-carbaldehyde and 3-ethoxy-2-hydroxybenzyl bromide are used as the starting materials, whereby the following compounds are obtained:

2,10-diethoxy-9-hydroxydibenzo[a,g] quinolizinium bromide, m.p. 232°–235° C (with decomposition);
Betaine, m.p. 280°–287° C (with decomposition);
Hydrochloride, m.p. 241°–243° C (with decomposition);
Nitrate, m.p. 227°–230° C (with decomposition);
Sulfate, m.p. 245°–247° C (with decomposition);
Phosphate, m.p. 237°–240° C (with decomposition);
Chloride of acetic ester, m.p. 209°–212° C (with decomposition);
Chloride of trichloroacetic acid, m.p. 215°–218° C (with decomposition);.

In the following examples, Example 5 is repeated except that appropriately substituted isoquinoline-1-carbaldoxime and appropiately substituted 2-hydroxy(or benzyloxy) benzyl halide are used as the starting materials.

EXAMPLE 15

2,9-dihydroxy-10-ethoxydibenzo[a,g] quinolizinium bromide, m.p. 201°-204° C (with decomposition);

Betaine, m.p. 240°-244° C (with decomposition);
Hydrochloride, m.p. 212°-215° C (with decomposition);
Nitrate, m.p. 220°-222° C (with decomposition);
Sulfate, m.p. 227°-230° C (with decomposition);
Phosphate, m.p. 218°-220° C (with decomposition);
Chloride of 9-acetic ester, m.p. 206°-208° C (with decomposition).

EXAMPLE 16

10-ethoxy-9-hydroxy-3-methoxydibenzo[a,g] quinolizinium bromide, m.p. 210°-212° C (with decomposition).

EXAMPLE 17

3,10-diethoxy-9-hydroxydibenzo[a,g] quinolizinium bromide, m.p. 222°-225° C (with decomposition).

EXAMPLE 18

3,9-dihydroxy-10-ethoxydibenzo[a,g] quinolizinium bromide, m.p. 200°-203° C (with decomposition).

EXAMPLE 19

9,10-dihydroxydibenzo[a,g] quinolizinium bromide, m.p. 197°-200° C (with decomposition);

Betaine, m.p. 260°-265° C (with decomposition);
Hydrochloride, m.p. 215°-217° C (with decomposition);
Nitrate, m.p. 203°-205° C (with decomposition);
Sulfate, m.p. 220°-222° C (with decomposition);
Phosphate, m.p. 212°-214° C (with decomposition);
Chloride of 9-acetic ester, m.p. 190°-193° C (with decomposition).

EXAMPLE 20

9,10-dihydroxy-1-methoxydibenzo[a,g] quinolizinium bromide, m.p. 232°-235° C ( with decomposition).

EXAMPLE 21

9,10-dihydroxy-2-methoxydibenzo[a,g] quinolizinium bromide, m.p. 215°-217° C (with decomposition);

Betaine, m.p. 271°-277° C (with decomposition);
Chloride, m.p. 221°-224° C (with decomposition);
Nitrate, m.p. 209°-121° C (with decomposition);
Sulfate, m.p. 223°-225° C (with decomposition);
Phosphate, m.p. 218°-220° C (with decomposition);
Chloride of 9-acetic ester, m.p. 201°-203° C (with decomposition);.

EXAMPLE 22

9,10-dihydroxy-3-methoxydibenzo[a,g] quinolizinium bromide, m.p. 216°-219° C (with composition).

EXAMPLE 23

9-hydroxy-2-methoxydibenzo[a,g] quinolizinium bromide, m.p. 226°-229° C (with decomposition);

Betaine, m.p. 272°-276° C (with decomposition);
Chloride, m.p. 237°-240° C (with decomposition);
Nitrate, m.p. 233°-236° C (with decomposition);
Sulfate, m.p. 216°-219° C (with decomposition);
Phosphate, m.p. 227°-230° C (with decomposition);
Chloride of acetic ester, m.p. 214°-217° C (with decomposition);.

EXAMPLE 24

2,9-dihydroxydibenzo[a,g] quinolizinium bromide, m.p. 185-188° C (with decomposition);

Betaine, m.p. 245°-250° C(with decomposition);
Chloride, m.p. 210°-212° C (with decomposition);
Nitrate, m.p. 214°-217° C(with decomposition);
Sulfate, m.p. 209°-212° C(with decomposition);
Phosphate, m.p. 200°-202° C(with decomposition);

EXAMPLE 25

9-hydroxy-3-methoxydibenzo[a,g] quinolizinium bromide, m.p. 191°-194° C(with decomposition).

EXAMPLE 26

3,9-dihydroxydibenzo[a,g] quinolizinium bromide, m.p. 215°-217° C(with decomposition).

EXAMPLE 27

9-hydroxy-4-methoxydibenzo[a,g] quinolizinium bromide, m.p. 193°-196° C(with decomposition);

Betaine, m.p. 257°-262° C(with decomposition);
Chloride, m.p. 203°-206° C(with decomposition);
Nitrate, m.p. 211°-213° C(with decomposition);
Sulfate, m.p. 230°-232° C(with decomposition);
Phosphate, m.p. 209°-211° C(with decomposition);
Chloride of acetic ester, m.p. 220°-223° C(with decomposition).

EXAMPLE 28

2,11-dimethoxy-9-hydroxydibenzo[a,g] quinolizinium bromide, m.p. 235°-237° C(with decomposition).

EXAMPLE 29

3,11-dimethoxy-9-hydroxydibenzo[a,g] quinolizinium bromide, m.p. 213°-215° C(with decomposition).

EXAMPLE 30

9-hydroxy-11-methoxydibenzo[a,g] quinolizinium bromide, m.p. 200°-203° C(with decomposition).

EXAMPLE 31

9,11-dihydroxydibenzo[a,g] quinolizinium bromide, m.p. 194°-198° C(with decomposition).

EXAMPLE 32

9,11-dihydroxy-2-methoxydibenzo[a,g] quinolizinium bromide, m.p. 228°-230° C(with decomposition).

EXAMPLE 33

9,11-dihydroxy-3-methoxydibenzo[a,g] quinolizinium bromide, m.p. 231°-234° C(with decomposition).

EXAMPLE 34

9-hydroxy-12-methyldibenzo[a,g] quinolizinium bromide, m.p. 225°-227° C (with decomposition);

Betaine, m.p. 268°-275° C(with decomposition);
Chloride, m.p. 230°-233° C(with decomposition);
Nitrate, m.p. 239°-242° C(with decomposition);
Sulfate, m.p. 235°-237° C(with decomposition);
Phosphate, m.p. 212°-215° C(with decomposition);.

EXAMPLE 35

9-hydroxy-2-methoxy-12-methyldibenzo[a,g] quinolizinium bromide, m.p. 217°-220° C(with decomposition);

Betaine, m.p. 254°-260° C(with decomposition);
Chloride, m.p. 221°-223° C(with decomposition);
Nitrate, m.p. 210°-213° C(with decomposition);
Sulfate, m.p. 234°-236° C(with decomposition);
Phosphate, m.p. 225°-227° C(with decomposition);
Chloride of acetic ester, m.p. 204°-206° C(with decomposition).

EXAMPLE 36

9-hydroxy-3-methoxy-12-methyldibenzo[a,g] quinolizinium bromide, m.p. 240°-242° C(with decomposition).

EXAMPLE 37

9,12-dihydroxydibenzo[a,g] quinolizinium bromide, m.p. 237°-240° C(with decomposition);

Betaine, m.p. 280°-285° C(with decomposition);
Chloride, m.p. 247°-250° C(with decomposition);
Nitrate, m.p. 231°-233° C(with decomposition);
Sulfate, m.p. 252°-255° C(with decomposition);
Phosphate, m.p. 240°-242° C(with decomposition);
Chloride of 9-acetic ester, m.p. 218°-220° C(with decomposition).

EXAMPLE 38

9,12-dihydroxy-2-methoxydibenzo[a,g] quinolizinium bromide, m.p. 216°-218° C(with decomposition);

Betaine, m.p. 266°-270° C(with decomposition);
Chloride, m.p. 220°-223° C(with decomposition);
Nitrate, m.p. 226°-228° C(with decompositin);
Sulfate, m.p. 234°-237° C(with decompositin);
Phosphate, m.p. 220°-222° C(with decomposition);
Chloride of 9-acetic ester, m.p. 207°-210° C(with decomposition).

EXAMPLE 39

9,12-dihydroxy-3-methoxydibenzo[a,g] quinolizinium bromide, m.p. 219°-221°0 C(with decomposition).

EXAMPLE 40

2,9-dihydroxy-3, 10-dimethoxydibenzo[a,g] quinolizinium bromide, m.p. 198°-203° C(with decomposition).

EXAMPLE 41

By following the procedure of Example 1 and substituting appropriately substituted isoquinoline-1-carbaldehydes and 2-hydroxybenzyl halides respectively for the starting materials, the following compounds are prepared:

10-methoxy-2,3, 9-trihydroxydibenzo[a,g] quinolizinium bromide, m.p. 203°-208° C(with decomposition).

2,9-dihydroxy-10-ethoxy-3-methoxydibenzo[a,g] quinolizinium bromide, m.p. 205°-210° C(with decomposition); chloride, m.p. 200°-205° C(with decomposition).

10-ethoxy-2,3,9-trihydroxydibenzo[a,g] quinolizinium bromide, m.p. 200°-208° C(with decomposition).

3,9-dihydroxy-10-ethoxy-2-methoxydibenzo[a,g] quinolizinium bromide, m.p. 198°-203° C(with decomposition).

9,11-dihydroxy-2,3-methylenedioxydibenzo[a,g] quinolizinium chloride, m.p. 215°-222° C(with decomposition); phosphate, m.p. 207°-210° C(with decomposition).

9-hydroxy-12-methyl-2,3-methylenedioxydibenzo[a,g] quinolizinium chloride, m.p. 243°-250° C(with decomposition); bromide, m.p. 271°-275° C(with decomposition).

9-hydroxy-2,3,11-trimethoxybenzyldibenzo[a,g] quinolizinium chloride, m.p. 208°-214° C(with decomposition). 2,3,11,12-bis(methylenedioxy)-9-hydroxydibenzo[a,g] quinolizinium chloride, m.p. 218°-221° C(with decomposition); sulfate, m.p. 205°-208° C(with decomposition).

9-hydroxy-12-propyl-1,2,3-trimethoxydibenzo[a,g] quinolizinium bromide, m.p. 253°-257° C(with decomposition).

3,9-dihydroxy-2,11,12-trimethoxydibenzo[a,g] quinolizinium bromide, m.p. 260°-264° C (with decomposition).

9-hydroxy-12-methylamino-2,3-methylenedioxydibenzo [a,g] quinolizinium bromide, m.p. 199°-203° C(with decomposition).

9hydroxy-12-methoxy-11-methyl-2,3-methylenedioxydibenzo[a,g] quinolizinium chloride, m.p. 231°-233° C(with decomposition).

9, 11, 12-trihydroxy-2,3-methylenedioxydibenzo[a,g] quinolizinium chloride, m.p. 213°-216° C(with decomposition).

11-amino-9-hydroxy-2,3-methylenedioxydibenzo[a,g] quinolizinium chloride, m.p. 247°-250° C(with decomposition).

9-hydroxy-2,3-methylenedioxy-1,11,12-trimethoxydibenzo[a,g] quinolizinium bromide, m.p. 188°-191° C(with decomposition).

9-hydroxy-2,3,4,11,12-pentamethoxydibenzo[a,g] quinolizinium bromide, m.p. 206°-208° C(with decomposition).

2,3-dimethoxy-11,12-dimethyl-9-hydroxydibenzo[a,g] quinolizinium acetate, m.p. 161°-169° C (with decomposition).

11,12-dimethyl-9-hydroxy-1,2,3-trimethoxydibenzo[a,g] quinolizinium bromide, m.p. 222°-226° C(with decomposition).

3,12-dimethoxy-9-hydroxy-2-methyldibenzo [a,g] quinolizinium bromide, m.p. 215°-217° C(with decomposition).

2,9-dihydroxy-3,11,12-trimethoxydibenzo[a,g] quinolizinium bromide, m.p. 233°-234° C(with decomposition).

2,9-dihydroxy-3,11-dimethoxydibenzo [a,g] quinolizinium bromide, m.p. 240°-245° C(with decomposition).

3,9-dihydroxy-2,12-dimethoxydibenzo[a,g] quinolizinium bromide, m.p. 205°-209 ° C(with decomposition).

3,9-dihydroxy-2,11,12-trimethoxydibenzo[a,g] quinolizinium bromide, m.p. 24°-243° C(with decomposition).

9-hydroxy-10-methoxy-11-methyl-2,3-methylenedioxydibenzo[a,g] quinolizinium bromide, m.p. 220°-225° C(with decomposition; chloride, m.p. 234°-240° C(with decomposition); phosphate, m.p. 211-215° C(with decomposition); sulfate, m.p. 241°-247°

C(with decomposition); nitrate, m.p. 222°-227° C(with decomposition).

9-hydroxy-10-methoxy-12-methyl-2,3-methylenedioxydibenzo[a,g] quinolizinium bromide, m.p. 225°-231° C(with decomposition); chloride, m.p. 239°-245° C(with decomposition); phosphate, m.p. 213°-218° C(with decomposition); sulfate, m.p. 238°-243° C(with decomposition); nitrate, m.p. 227°-232° C(with decomposition).

9-hydroxy-10-methoxy-12-methyl-1,2-methylenedioxydibenzo[a,g] quinolizinium bromide, m.p. 219°-225° C(with decomposition).

9-hydroxy-11-methyl-2,3, 10-trimethoxydibenzo[a,g] quinolizinium bromide, m.p. 215°-220° C(with decomposition).

9-hydroxy-12-methyl-2,3,10-trimethoxydibenzo[a,g] quinolizinium bromide, m.p. 214°-220° C(with decomposition).

1,11-dimethyl-9-hydroxy-2,3-methylenedioxydibenzo[a,g] quinolizinium bromide, m.p. 225°-231° C(with decomposition).

9,12-dihydroxy-10-methoxy-2,3-methylenedioxydibenzo[a,g] quinolizinium bromide, m.p. 209°-215° C(with decomposition).

10,11-dimethoxy-9-hydroxy-2,3-methylenedioxydibenzo[a,g] quinolizinium bromide, m.p. 252°-255° C(with decomposition); sulfate, m.p. 237°-241° C(with decomposition).

9,10-dihydroxy-2, 3-dimethoxydibenzo[a,g] quinolizinium bromide, m.p. 221°-230° C(with decomposition).

9,10-dihydroxy-2,3-methylenedioxydibenzo[a,g] quinolizinium bromide, m.p. 245°-247° C(with decomposition).

9-hydroxy-2,3-methylenedioxy-10,11,12-trimethoxydibenzo[a,g] quinolizinium bromide, m.p. 261°-263° C(with decomposition).

2,3-dimethoxy-9-hydroxy-12-methylaminodibenzo[a,g] quinolizinium bromide, m.p. 207°-210° C(with decomposition).

9-hydroxy-2,3,4,10-tetramethoxydibenzo[a,g] quinolizinium chloride, m.p. 161°-164° C(with decomposition).

12-amino-2,3-dimethoxy-9-hydroxydibenzo[a,g] quinolizinium chloride, m.p. 271°-274° C(with decomposition).

3,9-dihydroxy-2,10-dimethoxydibenzo[a,g] quinolizinium bromide, m.p. 207°-210° C(with decomposition).

3,9-dihydroxy-2,10,11-trimethoxydibenzo[a,g] quinolizinium bromide, m.p. 184°-191° C(with decomposition).

2,9-dihydroxy-3,10-dimethoxy-6-methyldibenzo[a,g] quinolizinium bromide, m.p. 212°-215° C(with decomposition).

2,9-dihydroxy-3,10,11-trimethoxydibenzo[a,g] quinolizinium bromide, m.p. 242°-248° C.

9-hydroxy-10-methoxy-5-methyl-1,2-methylenedioxydibenzo[a,g] quinolizinium bromide, m.p. 228°-233° C(with decomposition).

9-hydroxy-10-methoxy-2,3-methylenedioxy-5,6,11-trimethyldibenzo[a,g] quinolizinum bromide, m.p. 241°-245° C(with decomposition).

9-hydroxy-10-methoxy-1,2-methylenedioxydibenzo[a,g] quinolizinium bromide, m.p. 239°-246° C(with decomposition; chloride, m.p. 247°-251° C(with decomposition); phosphate, m.p. 227°-231° C(with decomposition); nitrate, m.p. 236-239° C(with decomposition); sulfate, m.p. 249°-256° C(with decomposition).

9-hydroxy-1,2,10-trimethoxydibenzo[a,g] quinolizinium bromide, m.p. 245°-248° C(with decomposition).

3,9-dihydroxy-2, 10-dimethoxy-1-methyldibenzo [a,g] quinolizinium bromide, m.p. 251°-254° C(with decomposition).

1,2-dimethyl-9-hydroxy-10-methoxydibenzo[a,g] quinolizinium bromide, m.p. 256°-259° C(with decomposition).

9-hydroxy-10-methoxy-1,2,3-trimethyldibenzo[a,g] quinolizinium bromide, m.p. 260°-261° C(with decomposition).

1,10-dimethoxy-9-hydroxy-2,3-methylenedioxydibenzo[a,g] quinolizinium bromide, m.p. 249°-255° C(with decomposition).

3,9-dihydroxy-10-methoxy-1,2-methylenedioxydibenzo[a,g] quinolizinium bromide, m.p. 243°-245° C(with decomposition).

2,3-ethylenedioxy-9-hydroxy-10-methoxy-1-methyldibenzo[a,g] quinolizinium bromide, m.p. 256°-263° C(with decomposition).

9-hydroxy-10-methoxy-4-methyl-2,3-methylenedioxydibenzo[a,g] quinolizinium bromide, m.p. 246°-250° C(with decomposition).

9-hydroxy-2,3,4,10-tetramethoxydibenzo[a,g] quinolizinium bromide, m.p. 241°-247° C(with decomposition).

9-hydroxy-10-methoxy-3,4-methylenedioxydibenzo [a,g] quinolizinium bromide, m.p. 239°-241° C(with decomposition); chloride, m.p. 246°-249° C (with decomposition); phosphate, m.p. 226°-229° C(with decomposition); nitrate, m.p. 239°-241° C(with decomposition; sulfate, m.p. 248°-251° C (with decomposition).

3,4-dimethyl-9-hydroxy-10-methoxydibenzo[a,g] quinolizinium bromide.

9-hydroxy-10-methoxy-2,3,4-trimethyldibenzo [a,g] quinolizinium bromide, m.p. 251°-257° C(with decomposition).

2,3-ethylenedioxy-9-hydroxy-10-methoxy-4-methyldibenzo[a,g] quinolizinium bromide, m.p. 250°-254° C(with decomposition).

2,10-dimethoxy-9-hydroxy-3,4-methylenedioxydibenzo[a,g] quinolizinium bromide, m.p. 241°-244° C(with decomposition).

1,9-dihydroxy-10-methoxy-3,4-methylenedioxydibenzo[a,g] quinolizinium bromide, m.p. 243°-248° C(with decomposition).

9-hydroxy-1, 3, 4, 10-tetramethoxydibenzo[a,g] quinolizinium bromide, m.p. 228°-231° C(with decomposition).

1,9-dihydroxy-3,4,10-trimethoxydibenzo[a,g] quinolizinium bromide, m.p. 208°-212° C(with decomposition).

9-hydroxy-10-methoxy-1,3,4-triethoxydibenzo[a,g] quinolizinium bromide, m.p. 200°-204° C(with decomposition).

4,10-dimethoxy-1,3,9-trihydroxydibenzo[a,g] quinolizinium bromide, m.p. 195°-200° C(with decomposition); chloride, m.p. 193°-195° C (with decomposition); sulfate, m.p. 235°-240° C(with decomposition); phosphate, m.p. 203°-209° C(with decomposition).

4,10-dimethoxy-9-hydroxy-1,2-methylenedioxydibenzo[a,g]quinolizinium bromide, m.p. 241°-245° C(with decomposition).

9-hydroxy-1,2,4,10-tetramethoxydibenzo[a,g] quinolizinium bromide, m.p. 232°–236° C(with decomposition).

1,9-dihydroxy-2,3,10-trimethoxydibenzo[a,g] quinolizinium bromide, m.p. 191°–194° C(with decomposition).

10-methoxy-1,2,4,9-tetrahydroxydibenzo[a,g] quinolizinium bromide, m.p. 209°–213° C(with decomposition).

1,10-dimethoxy-2,3,9-trihydroxydibenzo[a,g] quinolizinium bromide, m.p. 222°–224° C(with decomposition).

4,10-dimethoxy-1,2,9-trihydroxydibenzo[a,g] quinolizinium bromide, m.p. 206°–209° C(with decomposition); chloride, m.p. 200°–204° C(with decomposition); sulfate, m.p. 246°–250° C(with decomposition); phosphate, m.p. 212°–215° C(with decomposition).

9-hydroxy-2,3-methylenedioxy-1,4,10-trimethoxydibenzo[a,g] quinolizinium bromide, m.p. 269°–274° C(with decomposition); chloride, m.p. 247°–250° C(with decomposition); sulfate, m.p. 231°–233° C(with decomposition).

9-hydroxy-1,2,3,4,10-pentamethoxydibenzo[a,g] quinolizinium bromide, m.p. 241°–244° C(with decomposition).

10-methoxy-1,2,3,4,9-pentahydroxydibenzo [a,g] quinolizinium bromide, m.p. 279°–281° C 9-hydroxy-3,4,10-trimethoxy-1,2-methylenedioxydibenzo[a,g] quinolizinium bromide, m.p. 244°–246° C(with decomposition).

9-hydroxy-1-methyamino-2,3,4,10-tetramethoxydibenzo[a,g] quinolizinium bromide, m.p. 261°–263° C(with decomposition).

9-hydroxy-10-methoxy-1,2,3,4-tetraethoxydibenzo [a,g] quinolizinium bromide m.p. 224°–227° C(with decomposition).

9-hydroxy-10-methoxy-1,2,3,4-tetrapropoxydibenzo[a,g] quinolizinium bromide, m.p. 275°–279° C(with decomposition).

9-hydroxy-3, 4-methylenedioxy-1,2,10-trimethoxydibenzo[a,g] quinolizinium bromide, m.p. 288°–291° C(with decomposition).

2,3-ethylenedioxy-9-hydroxy-1,4,10-trimethoxydibenzo[a,g] quinolizinium bromide, m.p. 257°–260° C(with decomposition).

9-acetoxy-10,11-dimethoxy-2,3-methylenedioxydibenzo[a,g] quinolizinium chloride, m.p. 149°–152° C(with decomposition).

9-acetoxy-2,3,10,11-tetramethoxydibenzo[a,g] quinolizinium chloride, m.p. 174°–176° C(with decomposition).

9-acetoxy-1,2,3,10-tetramethoxydibenzo[a,g] quinolizinium chloride, m.p. 198°–202° C(with decomposition).

9-propionyloxy-10-methoxydibenzo[a,g] quinolizinium bromide;

9-carbamoyloxy-10-methoxydibenzo[a,g] quinolizinium bromide;

9-cinnamoyloxy10-methoxydibenzo[a,g] quinolizinium bromide;

9-trichloracetoxy-10-methoxydibenzo[a,g] quinolizinium bromide;

9-decanoyloxy-10-methoxydibenzo[a,g] quinolizinium bromide;

9-nicotinoyloxy-10-methoxydibenzo[a,g] quinolizinium bromide;

EXAMPLE 42

9-hydroxy-8-methyl-2,3,10-trimethoxydibenzo[a,g] quinolizinium bromide:

The procedure of Example 1 is repeated except that 6,7-dimethoxyisoquinoline-1-carbaldoxime and 1-(2-hydroxy-3-methoxyphenyl)-1-bromethane are used as the starting materials. Red crystals decomposing at 237°–243° C (methanol).

In like manner the following compounds are prepared:

9-hydroxy-8-methyl-2, 3-methylenedioxydibenzo[a,g] quinolizinium bromide.

EXAMPLE 43

3, 9-dihydroxy-2,10-dimethoxy-13-methyldibenzo[a,g] quinolizinium bromide;

The procedure of Example 1 is repeated except that 1-(1-hydroxyiminoethyl)-6-hydroxy-7-methoxyisoquinoline and 2-hydroxy-3-methoxybenzyl bromide are used as the starting materials. m.p.211°–217° C (with decomposition).

In like manner the following compounds are prepared:

8,13-dimethyl-9-hydroxy-2,3,10-trimethoxydibenzo[-a,g] quinolizinium bromide;

8,13-dimethyl-9-hydroxy-10-methoxy-2,3-methylenedioxydibenzo[a,g] quinolizinium bromide;

9-hydroxy-5,8,13-trimethyl-2,3-methylenedioxydibenzo[a,g] quinolizinium bromide;

9-hydroxy-8,13-dimethyl-2,3-methylenedioxydibenzo[-a,g] quinolizinium bromide;

2,9-dihydroxy-3,10-dimethoxy-8,13-dimethyldibenzo[-a,g] quinolizinium bromide;

9-hydroxy-10-ethoxy-13-methyldibenzo[a,g] quinolizinium bromide;

9-acetoxy-10-ethoxy-13-methyldibenzo[a,g] quinolizinium phosphate;

9-hydroxy-8-methyl-10-methoxydibenzo[a,g] quinolizinium bromide;

9-hydroxy-8-methyl-10-methoxy-2,3-methylenedioxydibenzo[a,g] quinolizinium phosphate;

9-acetoxy-8-methyl-10-methoxy-2,3-methylendioxydibenzo[a,g] quinolizinium chloride;

2,9-dihydroxy-3,10-dimethoxy-8-methyldibenzo[a,g] quinolizinium phosphate;

9-hydroxy-8-methyldibenzo[a,g] quinolizinium chloride;

3,9-dihydroxy-10-methoxy-8-methyldibenzo[a,g] quinolizinium phosphate;

9-acetoxy-10-methoxy-8-methyldibenzo[a,g] quinolizinium phosphate;

8,13-dimethyl-9-hydroxy-10-methoxydibenzo[a,g] quinolizinium phosphate;

8,13-dimethyl-9-hydroxydibenzo[a,g] quinolizinium phosphate.

Various other examples and modifications of the foregoing examples will be apparent to the person skilled in the art after reading the foregoing specification without departing from the spirit and scope of the invention. All such further examples and modifications are included within the scope of the appended claims.

What is claimed is:

1. A dibenzo(a,g) quinolizinium compound selected from the group consisting of a betaine of the formula:

I an anionide of the formula:

II and an O-acylate of the formula:

III wherein $R_5$, $R_6$, $R_8$ and $R_{13}$ are each hydrogen atom or lower alkyl; positions 1 to 4 and 10 to 12 on ring A and ring D respectively are each substituted with 0 to several substituents selected from the group consisting of lower alkyl, hydroxy, lower alkoxy, lower alkylenedioxy, amino and lower alkylamino; with the proviso that when $R_8$ is hydrogen atom and ring D is substituted only at position 10 with alkoxy, ring A cannot be substituted only at positions 2 and 3 with alkoxy or alkylenedioxy; X is a pharmaceutically acceptable anion; and RCO is an acyl group derived from an aliphatic or araliphatic carboxylic acid.

2. A compound of claim 1 of the formula:

I wherein symbols and rings are as defined.

3. A compound of claim 1 of the formula:

II wherein symbols and rings are as defined.

4. A compound of claim 1 of the formula:

III wherein symbols and rings are as defined.

5. As a compound of claim 3, 9-hydroxydibenzo[a,g] quinolizinium anionide.

6. As a compound of claim 3, 9-hydroxy-10-methoxydibenzo[a,g] quinolizinium anionide.

7. As a compound of claim 3, 9-hydroxy-11-methoxydibenzo[a,g] quinolizinium anionide.

8. As a compound of claim 3, 9-hydroxy-10-ethoxydibenzo[a,g] quinolizinium anionide.

9. As a compound of claim 3, 3, 9-dihydroxy-0-methoxydibenzo[a,g] quinolizinium anionide.

10. As a compound of claim 3, 9, 10-dihydroxy-3-methoxydibenzo[a,g] quinolizinium anionide.

11. As a compound of claim 3, 9-hydroxy-2, 10-dimethoxydibenzo[a,g] quinolizinium anionide.

12. As a compound of claim 3, 9-hydroxy-10-methoxy-8-methyldibenzo[a,g] quinolizinium anionide.

13. As a compound of claim 3, 9-hydroxy-10-methoxy-13-methyldibenzo[a,g] quinolizinium anionide.

14. As a compound of claim 3, 9-hydroxy-10-methoxy-8, 13-dimethyldibenzo [a,g] quinolizinium anionide.

15. As a compound of claim 2, 9-hydroxy-10-methoxydibenzo[a,g] quinolizinium betaine.

16. As a compound of claim 4, 9-acetoxy-10-methoxydibenzo[a,g] quinolizinium anionide.

* * * * *

UNITED STATES PATENT AND TRADEMARK OFFICE
CERTIFICATE OF CORRECTION

PATENT NO. : 4,042,592
DATED : August 16, 1977
INVENTOR(S) : YOSHIO SAWA

It is certified that error appears in the above-identified patent and that said Letters Patent are hereby corrected as shown below:

Claim 9: should read -- As a compound of claim 3, 3, 9-dihydroxy-10-methoxydibenzo[a,g] quinolizinium anionide. --

Signed and Sealed this

First Day of November 1977

[SEAL]

Attest:

RUTH C. MASON
*Attesting Officer*

LUTRELLE F. PARKER
*Acting Commissioner of Patents and Trademarks*